United States Patent [19]

Desmond et al.

[11] Patent Number: 4,681,747

[45] Date of Patent: * Jul. 21, 1987

[54] PROCESS FOR THE PREPARATION OF METALLOSILICATES OF TETRAVALENT LANTHANIDE AND ACTINIDE SERIES METALS USING HETERPOLY METALLATES

[75] Inventors: Michael J. Desmond, Cleveland hts.; Janie K. Currie, Novelty; Frederick A. Pesa, Aurora, all of Ohio

[73] Assignee: The Standard Oil Company, Cleveland, Ohio

[ * ] Notice: The portion of the term of this patent subsequent to Jan. 14, 2003 has been disclaimed.

[21] Appl. No.: 672,594

[22] Filed: Nov. 16, 1984

[51] Int. Cl.$^4$ .................................................. C01B 35/10
[52] U.S. Cl. .................................. 423/277; 423/326; 423/328; 423/329; 423/330; 423/331; 423/332; 502/60; 502/62; 502/65; 502/71; 502/73; 502/77; 502/202
[58] Field of Search ............... 423/326, 277, 328, 329; 502/60, 77

[56] References Cited

U.S. PATENT DOCUMENTS

| | | | |
|---|---|---|---|
| Re. 29,948 | 3/1979 | Dwyer et al. | 423/328 |
| 4,163,028 | 7/1979 | Tabak et al. | 585/488 |
| 4,188,282 | 2/1980 | Tabak et al. | 208/134 |
| 4,564,511 | 1/1986 | Desmond et al. | 423/329 |
| 4,576,805 | 3/1986 | Chang et al. | 502/77 |
| 4,594,146 | 6/1986 | Chester et al. | 502/55 |

FOREIGN PATENT DOCUMENTS

| | | | |
|---|---|---|---|
| 0007817 | 1/1982 | Japan | 423/328 |
| 0007818 | 1/1982 | Japan | 423/328 |
| 2024790 | 1/1980 | United Kingdom | 423/328 |
| 2033358 | 5/1980 | United Kingdom | 423/328 |

*Primary Examiner*—John Doll
*Assistant Examiner*—Jackson Leeds
*Attorney, Agent, or Firm*—Sue E. Phillips; Joseph G. Curatolo; Larry W. Evans

[57] ABSTRACT

A molecular sieving metallosilicate is disclosed which comprises a complex represented in terms of mole ratios of oxides by the formula:

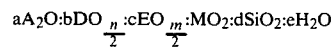

$$aA_2O:bDO_{n/2}:cEO_{m/2}:MO_2:dSiO_2:eH_2O$$

wherein A is an ammonium, alkyl ammonium, alkyl phosphonium or alkyl arsonium ion; D is an alkali or alkaline earth metal ion or a mixture of two or more thereof; E is selected from the group consisting of Al, B, Mo, W, Fe, or a mixture of two or more thereof; M is a tetravalent metal selected from the Lanthanide or Actinide series; a is a number ranging from zero to about 25; b is a number ranging from zero to about 1.5; c is a number ranging from zero to about 0.3; d is a number ranging from about 20 to about 500; e is a number ranging from zero to about 200. The X-ray diffraction pattern for these metallosilicates indicates a ZSM-5 like crystalline structure. A method for making these metallosilicates, and a method for dehydrating and reforming methanol using these metallosilicates are disclosed.

32 Claims, No Drawings

PROCESS FOR THE PREPARATION OF METALLOSILICATES OF TETRAVALENT LANTHANIDE AND ACTINIDE SERIES METALS USING HETERPOLY METALLATES

TECHNICAL FIELD

This inventiion relates to molecular sieves and, more particularly, to molecular sieving metallosilicates of tetravalent Lanthanide and Actinide series metals. This invention also relates to a method for making such molecular sieving metallosilicates, and a method for converting methanol to olefins using such metallosilicates.

BACKGROUND OF THE INVENTION

The term "molecular sieve" refers to a wide variety of positive ion containing crystalline materials of both natural and synthetic varieties which exhibit the property of acting as sieves on a molecular scale. A major class of molecular sieves are crystalline aluminosilicates, although other crystalline materials are included in the broad definition. Examples of such other crystalline materials include coal, special active carbons, porous glass, microporous beryllium oxide powders, and layer silicates modified by exchange with organic cations. See, D. W. Breck, "Zeolite Molecular Sieves: Structure, Chemistry, and Use", John Wiley & Sons, 1974.

Zeolites are crystalline, hydrated, framework aluminosilicates which are based on a three-dimensional network of $AlO_4$ and $SiO_4$ tetrahedra linked to each other by sharing all of the oxygens.

Zeolites may be represented by the empirical formula

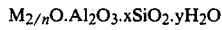

$$M_{2/n}O \cdot Al_2O_3 \cdot xSiO_2 \cdot yH_2O$$

wherein, x is generally equal to or greater than 2 since $AlO_4$ tetrahedra are joined only to $SiO_4$ tetrahedra, and n is the cation valence. The framework contains channels and interconnected voids which are occupied by the cation, M, and water molecules. The cations may be mobile and exchangeable to varying degrees by other cations. Intracrystalline zeolitic water in many zeolites is removed continuously and reversibly. In many other zeolites, mineral and synthetic, cation exchange or dehydration may produce structural changes in the framework. Ammonium and alkylammonium cations may be incorporated in synthetic zeolites, e.g., $NH_4$, $CH_3NH_3$, $(CH_3)_2NH_2$, $(CH_3)_3NH$, and $(CH_3)_4N$. In some synthetic zeolites, aluminum cations may be substituted by gallium ions and silicon ions by germanium or phosphorus ions. The latter necessitates a modification of the structural formula.

The structural formula of a zeolite is best expressed for the crystallographic unit cell as: $M_{x/n}[(AlO_2)_x(SiO_2)_y] \cdot wH_2O$ where M is the cation of valence n, w is the number of water molecules and the ratio y/x usually has values of 1–100 depending upon the structure. The sum (x+y) is the total number of tetrahedra in the unit cell. The complex within the [ ] represents the framework composition.

The zeolites described in the patent literature and published journals are designated by letters or other convenient symbols. Exemplary of these materials are Zeolite A (U.S. Pat. No. 2,882,243), Zeolite X (U.S. Pat. No. 2,882,244), Zeolite Y (U.S. Pat. No. 3,130,007), Zeolite ZSM-5 (U.S. Pat. No. 3,702,886), Zeolite ZSM-11 (U.S. Pat. No. 3,709,979), and Zeolite ZSM-12 (U.S. Pat. No. 3,832,449).

Although there are 34 species of zeolite minerals and about 100 types of synthetic zeolites, only a few have been found to have practical significance. Many of the zeolites, after dehydration, are permeated by very small channel systems which are not interpenetrating and which may contain serious diffusion blocks. In other cases dehydration irreversibly disturbs the framework structure and the positions of metal cations, so that the structure partially collapses and dehydration is not completely reversible. To be efficiently used as a molecular sieve, the structure of the zeolite after complete dehydration must remain intact.

There has been considerable interest in developing metallosilicates other than aluminosilicates which exhibit molecular sieve characteristics. For example, U.S. Pat. Nos. 3,329,480 and 3,329,481 disclose crystalline zircano-silicates and titano-silicates, respectively. U.S. Pat. No. 3,329,384 discloses group IV-B metallosilicates. U.S. Pat. Nos. 4,208,305, 4,238,315 and 4,337,176 disclose iron silicates. U.S. Pat. No. 4,329,328 discloses zinco-, stanno-, and titano-silicates. European patent applications Nos. 0 038 682 and 0 044 740 disclose cobalt silicates. European patent application No. 0 050 525 discloses nickel silicate.

U.K. patent application No. GB 2,024,790 A discloses a silica-based material which has been modified with one or more elements which have entered the crystalline lattice of the silica in place of silicon atoms of the silica or in the form of salts of bisilicic or polysilicic acids. The elements identified as being suitable for making such silica-based materials are chromium, beryllium, titanium, vanadium, manganese, iron, cobalt, zinc, zirconium, rhodium, silver, tin, antimony and boron.

U.S. Pat. No. 4,299,808 discloses chromosilicates formed by reacting an aqueous mixture of an oxide of silicon, a compound of chromium, a hydroxide of an alkali or an alkaline earth metal, and an alkylammonium cation or a precursor of an alkylammonium cation.

U.S. Pat. Nos. 3,769,386, 4,192,778 and 4,339,354 relate to rare earth metal containing silicates. U.S. Pat. No. 3,769,386 discloses zeolitic alumino-metallosilicates crystallized from an aqueous reaction mixture containing $Na_2O$, $SiO_2$, $Al_2O_3$ and $R_{2/n}$ wherein R is Mg, Ca, Y, Fe, Co, Ni or a rare earth metal and n is the valence of R. U.S. Pat. No. 4,192,778 discloses rare earth exchanged zeolites of the faujasite type in which the equivalent of Na is less than 0.1 and the rare earth is at least 0.9 equivalents per gram atom of aluminum. U.S. Pat. No. 4,339,354 discloses a catalyst comprising a crystalline aluminosilicate such as zeolite Y, an inorganic matrix, and discrete particles of alumina, the catalyst having specified alkali metal and rare earth metal contents.

There remains a need for suitable metallosilicates that exhibit molecular sieve character and employ tetravalent metals of the Lanthanide or Actinide series in their crystalline framework. There is also a need for a relatively simplified method for making such metallosilicates.

SUMMARY OF THE INVENTION

The present invention relates to metallosilicates which exhibit molecular sieve character and employ tetravalent Lanthanide or Actinide series metals in their crystalline framework. The invention also relates to a relatively simplified method for making such metallosilicates, and a method for converting methanol to olefins using such metallosilicates.

Broadly stated, the present invention contemplates the provision of a molecular sieving metallosilicate comprising a complex represented in terms of mole ratios of oxides by the formula $$aA_2O:bDO:cEO_{n/2}:MO_2:dSiO_2:eH_2O$$

wherein
- A is an ammonium, alkyl ammonium, alkyl phosphonium or alkyl arsonium ion;
- D is an alkali or alkaline earth metal ion, or a mixture of two or more thereof;
- E is selected from the group consisting of Al, B, Mo, W, Fe, or a mixture of two or more thereof;
- M is a tetravalent metal selected from the Lanthanide or Actinide series;
- a is a number ranging from zero to about 25;
- b is a number ranging from zero to about 1.5;
- c is a number ranging from zero to about 0.3;
- d is a number ranging from about 20 to about 500; and
- e is a number ranging from zero to about 200.

The X-ray diffraction pattern for these metallosilicates indicates ZSM-5 like crystalline structures.

The invention further provides for a method for preparing a molecular sieving metallosilicate comprising the following steps:

(A) providing a mixture comprising: (1) water; (2) an oxide of silicon source; (3) a synthesis directing agent and/or a mineralizing agent; and (4) a tetravalent Lanthanide or Actinide series metal containing compound; and (B) maintaining said mixture at a temperature in the range of about 80° C. to about 300° C. for an effective period of time to provide said metallosilicate.

The invention also provides for a method for dehydrating and reforming methanol with the above-indicated metallosilicates.

DETAILED DESCRIPTION OF THE PREFERRED EMBODIMENT

The molecular sieving metallosilicates provided in accordance with the invention are tetravalent Lanthanide or Actinide series metal containing complexes represented in terms of mole ratios of oxides by the formula $$aA_2O:bDO:cEO_{n/2}:MO_2:dSiO_2:eH_2O$$

wherein
- A is an ammonium, alkyl ammonium, alkyl phosphonium or alkyl arsonium ion; preferably ammonium, or tetraalkyl (e.g., tetrapropyl) ammonium, phosphonium or arsonium;
- D is an alkali or alkaline earth metal ion or a mixture of two or more thereof, preferably sodium;
- E is selected from the group consisting of Al, B, Mo, W, Fe or a mixture of two or more thereof, and is preferably Mo or W;
- M is a tetravalent element selected from the Lanthanide or Actinide series, preferably Ce, Th, U, Pr, Tb, Pa, Np, Pu, Am or a mixture of two or more of said metals, and most preferably Th, U, Ce, Pr or a mixture of two or more thereof;
- a is a number ranging from zero to about 25, preferably from zero to about 12;
- b is a number ranging from zero to about 1.5;
- c is a number ranging from zero to about 0.3, preferably from zero to about 0.2;
- d is a number ranging from about 20 to about 500, preferably from about 30 to about 200;
- e is a number ranging from zero to about 200, preferably from zero to about 80.

The X-ray diffraction patterns for these metallosilicates as synthesized show at least the following significant lines:

TABLE I

| Interplanar Spacing d(A) | Relative Intensity |
|---|---|
| 11.25 ± 0.2 | s. |
| 10.1 ± 0.2 | m.-s. |
| 7.55 ± 0.15 | w. |
| 6.40 ± 0.10 | w. |
| 4.61 ± 0.08 | w. |
| 3.84 ± 0.08 | s. |
| 3.73 ± 0.05 | s. |
| 3.65 ± 0.05 | m.-s. |
| 3.05 ± 0.03 | w. |
| 2.99 ± 0.02 | w. |
| 2.00 ± 0.02 | w. |

The values were determined by standard techniques. In Table I, the relative intensities are given in terms of symbols: s.=strong, m.=medium, and w.=weak.

The mixture provided for in step (A) of the process of the invention for making the metallosilicates is preferably prepared in three steps. First, the oxide of silicon source and preferably a synthesis directing agent are mixed in water to provide a first mixture. This first mixture is preferably in the form of a colloidal dispersion. Second, the oxide, hydroxide, alkoxide, salt or heteropolymetallate of the tetravalent Lanthanide or Actinide series metal is mixed with water and preferably a mineralizing agent to provide a second mixture. This second mixture is usually in the form of a dispersion or solution. Third, these first and second mixtures are mixed together to form a third mixture.

This third mixture which is in the form of a gel is the mixture called for in step (A) of the inventive method. Stirring or agitation is generally required to effect a homogeneous mixture. The Si to tetravalent Lanthanide or Actinide series metal mole ratio for this third mixture is preferably in the range of about 20 to about 200. The OH⁻ to Si mole ratio is preferably in the range of about 0.1 to about 10. The H₂O to OH⁻ mole ratio is preferably in the range of about 10 to about 1000. The Si to mineralizing agent plus synthesis directing agent mole ratio is preferably in the range of about 0.1 to about 30.

The oxide of silicon source can be any source that provides silicon oxide, hydroxide or alkoxide. Such sources include silica gel, silicic acid, silica sol and the silicates. Included within the silicates are the alkali and alkaline earth metal silicates with sodium silicate and potassium silicate being preferred. The alkoxides include those alkoxides of up to about 10, preferably up to about 6 carbon atoms. The silica sols are aqueous colloidal dispersions containing colloidal silica particles. The solids content of these colloidal dispersions generally ranges up to about 70% by weight, and is preferably in the range of about 5% to about 50%. These dispersions usually include an effective amount of an anionic (e.g., acetate, halogen, etc.) or cationic (e.g., alkali metal, ammonium, etc.) stabilizing agent to stabilize the dispersion. Generally the level of addition of such stabilizing agents is up to about 10% by weight of the solids in the dispersion. A commercially available silica sol that is particularly useful is Ludox AS-40 which is a product of DuPont identified as an ammonium stabilized silica sol containing 40% by weight silica.

The synthesis directing agent can be but is not limited to being a templating agent. This agent can be the cation of an amine or alkanol amine compound, alkyl substituted amine or alkyl substituted alkanol amine compound, ammonium or alkyl ammonium compound, or alkyl phosphonium or alkyl arsonium compound. Alkyl groups, if present, have up to about six carbon atoms each. The alkyl ammonium, alkyl phosphonium and alkyl arsonium compounds can be mono-, di-, tri- or tetra-alkyl compounds, and in cases wherein more than one alkyl group is present the alkyl groups can be the same or different. These compounds include the oxides, hydroxides, inorganic salts (e.g., nitrates, phosphates, sulfates, halides, carbonates, and the like) as well as the organic salts, (e.g., acetates, formates, butyrates, propionates, benzylates and the like). Preferred alkyl ammonium, alkyl phosphonium and alkyl arsonium compounds are the tetraalkyl-(e.g., tetrapropyl)ammonium hydroxides and halides (e.g., bromide). The amines, alkyl substituted amines, alkanol amines and alkyl substituted alkanol amines include primary, secondary and tertiary mono- and poly-amines of up to about six carbon atoms. The alkanol amines and alkyl substituted alkanol amines can be monohydric or polyhydric. Examples include methyl- and ethyl amine, dimethyl- and diethyl-amine, trimethyl- and triethyl amine, diethylmethyl amine, 2-hdyroxyethylamine, 3-hydroxybutyl amine, diethanolamine, diethylethanol amine, di-(2-hydroxypropyl amine), N,N,N'-tri-(hydroxy methyl)ethylene-diamine, etc.

The mineralizing agent is an alkali or alkaline earth metal compound. These compounds include the oxides, hydroxides, inorganic salts (e.g., nitrates, phosphates, halides, carbonates, silicates, aluminates and the like) as well as the organic salts, (e.g., acetates, formates, butyrates, propionates, benzylates and the like). A preferred mineralizing agent is sodium hydroxide.

The tetravalent Lanthanide and Actinide series metal containing compounds are preferably oxides, hydroxides, alkoxides, salts or heteropolymetallates of said metals. The alkoxides include those alkoxides of up to about 10, preferably up to about 6 carbon atoms per alkyl group. The salts include the inorganic salts (e.g., nitrates, phosphates, halides, carbonates, silicates, aluminates and the like) as well as the organic salts, (e.g., acetates, formates, butyrates, propionates, benzylates, tartrates and the like).

The heteropolymetallates can be represented by the formula

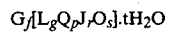

wherein
G is an ion selected from the group consisting of hydrogen, Group I-A, II-A, I-B or II-B metals, ammonium, alkyl ammonium, alkyl phosphonium or alkyl arsonium, or a mixture of two or more thereof;
L is P, As, Si, Ge, Al, H or a mixture of two or more thereof;
Q is said tetravalent Lanthanide or Actinide series metal;
J is Mo, W, V or Nb or a mixture of two or more thereof;
f is a number which when multiplied by the charge of G will result in balancing the charge on the complex within the brackets;
g is a number ranging from zero to about 20;
p is a number ranging from zero to about 20;
r is a number ranging from about 1 to about 50;
s is a number ranging from about 7 to about 150; and
t is a number ranging from zero to about 150.

G is preferably H, Na, K, NH$_4$, or a mixture thereof. L is preferably P or Ge or a mixture thereof. Q is preferably Ce, Pr, Tb, Th, Pa, U, Np, Pu, Am or a mixture thereof, and most preferably Ce, Th, U, Pr or a mixture thereof. J is preferably Mo or W. The alkyl group on the alkyl ammonium, alkyl arsonium and alkyl phosphonium can have up to about 6 carbon atoms. The alkyl ammonium, alkyl phosphonium and alkyl arsonium compounds can be mono-, di-, tri- or tetra-alkyl compounds, and when more than one alkyl group is present they can be the same or different.

Exemplary heteropolymetallates that are useful include

(1)

wherein: Q is Ce, Th, U, Pr or a mixture of two or more thereof; J is Mo or W; and G, f and t are as defined above.

(2)

wherein: L is P, Ge or a mixture thereof; J is Mo or W; Q is Ce, Pr, Tb, Th, Pa, U, Np, Pu, Am or a mixture of two or more thereof; and G, f and t are as defined above.

(3)

wherein: L is P, Ge or a mixture thereof; J is Mo or W; Q is Ce, Pr, Tb, Th, Pa, U, Np, Pu, Am or a mixture of two or more thereof; and G, f and t are as defined above.

In the method of the present invention for making the metallosilicates, the mixture provided for in step (A) containing water, the oxide of silicon source, mineralizing and/or synthesis directing agent, and tetravalent Lanthanide or Actinide metal containing compound is thoroughly mixed and then placed in a reactor. The reactor is preferably an enclosed reactor (e.g., a static bomb style reactor). The contents are heated to a temperature in the range of about 80° C. to about 300° C., preferably about 125° C. to about 200° C., for an effective period of time to provide the desired molecular sieving metallosilicate, preferably for about 4 hours to about 30 days, more preferably about one to about ten days. The pressure within the reactor is preferably at at least the vapor pressure of water at the temperature of the reactor contents. The contents of the reactor are then allowed to cool to room temperature. The crystalline solids are separated from the mother liquor and washed thoroughly with water. Separation can be effected by conventional filtration techniques. The crystalline solids are then allowed to dry in air, such solids being the desired molecular sieving metallosilicates of the invention.

The metallosilicates can be heat treated at a temperature of about 300° C. to about 900° C., preferably about 400° C. to about 600° C. in an inert, oxidizing or reducing atmosphere for a sufficient time to pyrolyze any synthesis directing agent intermixed with such metallosilicates. The time period for this heat treating step is dependent upon the mass of material being treated. Preferably the heat treating step is conducted for at least about 30 minutes, but this time period can be more or less than 30 minutes depending upon the mass of material being treated. The inert atmosphere is preferably nitrogen, argon, helium or neon. The reducing atmosphere is hydrogen or a mixture of hydrogen and one of the above-indicated inert gases. The reducing atmosphere can thus contain from about 1% to about 100% hydrogen, preferably about 1% to about 20% hydrogen, with the remainder being inert gas. The oxidizing atmosphere can be oxygen or a mixture of oxygen and one of the above-indicated inert gases. The oxidizing atmosphere can thus contain from about 1% to about 100% oxygen, preferably from about 1% to about 20% oxygen with the remainder being inert gas. A preferred oxidizing atmosphere is air. The X-ray diffraction pattern for these heat-treated metallosilicates show the following significant lines:

| Interplanar Spacing d(A) | Relative Intensity |
| --- | --- |
| 11.2 ± 0.2 | s. |
| 10.2 ± 0.2 | s. |
| 6.74 ± 0.1 | w. |
| 6.38 ± 0.1 | w. |
| 6.01 ± 0.08 | w. |
| 5.75 ± 0.08 | w. |
| 5.61 ± 0.08 | w. |
| 4.38 ± 0.06 | w. |
| 3.86 ± 0.05 | s. |
| 3.84 ± 0.05 | s. |
| 3.73 ± 0.05 | s. |
| 3.66 ± 0.04 | w.-m. |
| 3.00 ± 0.02 | w. |
| 2.015 ± 0.01 | w. |
| 1.995 ± 0.01 | w. |

The metallosilicates of the invention can be cation exchanged with an ammonium salt or a salt of a catalytically active metal. The salt of the catalytically active metal is preferably the salt of a Group VII, IB or IIB metal, with zinc, copper, nickel, cobalt and iron being preferred. The anionic portions of these salts include the nitrates, phosphates, sulfates, acetates and halides. The cation exchange procedure employed herein is entirely conventional. Briefly, the metallosilicate and the ammonium salt or salt of catalytically active metal are dispersed in water for a few minutes to several hours, preferably about one to about ten hours, and maintained at about room temperature to about the boiling point of the water, then filtered and washed, with the result being the formation of such cation-exchanged metallosilicates.

Optionally, the cation-exchanged metallosilicates can be heat treated in an inert, oxidizing or reducing atmosphere using the heat treating procedures described above to convert the cation-exchanged species to a more active form. This heat treating procedure is particularly suitable for driving off ammonia from an ammonium-metallosilicate to convert such metallosilicate to the acid form.

An advantage of the present invention is that radioactive isotopes of the Lanthanide and Actinide series metals can be included in the synthesis of the metallosilicates of the invention, and thus such radioactive isotopes can be trapped within the stable metallosilicate structures provided herein. Thus the present invention provides a direct method for the encapsulation of such radioactive isotopes.

The metallosilicates of the present invention can be used in many of the known applications for zeolites and molecular sieves. The crystalline structure of these metallosilicates make them particularly suitable as catalysts and adsorbents.

The metallosilicates of the invention are particularly suitable for the reforming and dehydration of methanol by contacting one of said metallosilicates with methanol at an elevated temperature. The product produced thereby is typically a hydrocarbon mixture containing a mixture of paraffins and olefins of about six or less carbon atoms, dimethyl ether, carbon monoxide and carbon dioxide. The methanol reactant can be in the form of pure methanol or it can be mixed with an inert gas such as nitrogen, argon, helium or neon. The reaction can be carried out in either a fluidized-bed mode or fixed-bed mode, continuously or in batch operation. The liquid hourly space velocity (LHSV) of the reactants is not critical but should be from about 0.01 to about 100, preferably from about 0.05 to about 10 liters of reactant per liter of catalyst per hour. The partial pressure of methanol over the catalyst should normally be atmospheric or subatmospheric. The reaction temperature should be maintained from about 250° C. to about 600° C., preferably from about 300° C. to about 500° C. The contact time of reactant with catalyst is generally from about 0.1 seconds to about 40 seconds, preferably from about 1 second to about 10 seconds.

The product selectivities on a per carbon atom basis from the converted methanol using the metallosilicates of the invention typically are the following:

| Component | Percent on a Per Carbon Basis |
| --- | --- |
| Methane | about 2 to about 30% |
| Ethane | about 0 to about 5% |
| Propane | about 0 to about 10% |
| Butanes | about 2 to about 10% |
| Pentanes | about 1 to about 10% |
| Ethylene | about 0 to about 5% |
| Propylenes | about 2 to about 20% |
| Butylenes | about 2 to about 15% |
| Pentenes | about 1 to about 10% |
| $C_6$ + Hydrocarbon | about 1 to about 20% |
| Dimethyl Ether | about 20 to about 80% |
| Carbon Monoxide | about 1 to about 20% |
| Carbon Dioxide | about 0 to about 5% |

In order to further illustrate the present invention, the following examples are provided. Unless otherwise indicated, in the following examples as well as throughout the specification and in the claims, all parts and percentages are by weight, and all temperatures are in degrees centigrade.

EXAMPLE 1

11.84 parts of Ludox AS-40 and 2.7 parts of tetrapropyl ammonium bromide were mixed in a polypropylene beaker to form a first mixture. 2.0 parts of $(NH_4)_8[Mo_{12}ThO_{42}] \cdot tH_2O$ were mixed with 4.0 parts of water with stirring in another polypropylene beaker to form a second mixture. 2.0 parts of a 50% sodium hydroxide solution were added to the second mixture. The two mixtures were mixed together with the result being the formation of a gel. The gel was stirred to homogenize the gel. The Si/Mo mole ratio was 14.5. The Si/Th mole ratio was 170. The Si/Na mole ratio was 3.16. Two 9 part samples of the gel were placed in Teflon-lined stainless steel bombs. The bombs were placed in an oven at a temperature of 150° C. The samples were recovered after 12 days and 18 days. The crystalline solids were separated from the mother liquor by filtering. The solids were washed in water and a 10% hydrochloric acid solution, then dried in air. The X-ray diffraction patterns of the as recovered samples exhibited the following significant lines (CuK$_\alpha$ radiation):

| Interplanar Spacing d(A) | Relative Intensity |
|---|---|
| 11.4 | s. |
| 10.2 | s. |
| 9.15 | w. |
| 7.59 | w. |
| 6.45 | w. |
| 5.03 | w. |
| 4.65 | w. |
| 3.86 | s. |
| 3.79 | s. |
| 3.75 | s. |
| 3.68 | m. |
| 3.07 | w. |
| 3.00 | w. |
| 2.98 | w. |
| 2.02 | w. |
| 2.00 | w. |

EXAMPLE 2

The 12 and 18 day samples from Example 1 were heated in air at 550° C. for four hours. The 12-day sample had the following analysis: 42% Si; 0.05% Al; 0.17% Na; 0.08% Mo; and 2.4% Th. The mole ratio for the 12-day sample were: Si/Th=150; Na/Th=0.7; Mo/Th=0.1; and Al/Th=0.18. The 18-day sample had the following analysis: 38% Si; 0.05% Al; 0.16% Na; 0.04% Mo; and 3.3% Th. The mole ratios for the 18-day sample were: Si/Th=96; Na/Th=0.43; Mo/Th=0.03; and Al/Th=0.13. The X-ray diffraction patterns of the recovered solid products exhibited the following significant lines (CuK$_\alpha$ radiation):

| Interplanar Spacing d(A) | Relative Intensity |
|---|---|
| 11.2 | s. |
| 10.1 | s. |
| 6.71 | w. |
| 6.38 | w. |
| 6.01 | w. |
| 5.74 | w. |
| 5.60 | w. |
| 5.05 | w. |
| 4.62 | w. |
| 3.86 | s. |
| 3.84 | s. |
| 3.76 | s. |
| 3.72 | s. |
| 3.67 | m. |
| 3.05 | w. |
| 2.99 | w. |
| 2.01 | w. |
| 1.99 | w. |

EXAMPLE 3

11.84 parts of Ludox AS-40 and 1.1 parts of tetrapropyl ammonium bromide (TPABr) were mixed in a polypropylene beaker to form a first mixture. 0.68 parts of Na$_2$C$_2$H$_4$O$_6$.2H$_2$O and 0.50 parts of ThCl$_4$ were mixed with 2.0 parts of a 50% sodium hydroxide solution to form a second mixture. The two mixtures were mixed together with the result being the formation of a gel. The gel was stirred to homogenize the gel. The Si/Th mole ratio was 59. The Si/TPABr mole ratio was 19.3. The Si/Na mole ratio was 2.55. The mixture was divided into two equal samples, and each sample was placed in a Teflon-lined stainless steel bomb. The bombs were placed in an oven at a temperature of 150° C. The samples were recovered after 7 days and 14 days. The solids were recovered from the mother liquor by filtering. The solids were washed thoroughly with water and then dried in air. The 7-day sample had the following analysis: 28% Si; 4.6% Th; 1.2% Na; and 0.02% Al. The mole ratios for this sample were: Si/Th=50.4; Na/Th=2.6; and Al/Th=0.04. The X-ray diffraction pattern for the samples had the following significant lines (CuK$_\alpha$ radiation):

| Interplanar Spacing d(A) | Relative Intensity |
|---|---|
| 11.24 | s. |
| 9.99 | m. |
| 7.45 | w. |
| 6.38 | w. |
| 4.60 | w. |
| 3.84 | s. |
| 3.72 | s. |
| 3.65 | s. |
| 3.05 | w. |
| 2.98 | w. |
| 2.00 | w. |

EXAMPLE 4

23.68 parts of Ludox AS-40 and 2.2 parts of tetrapropyl ammonium bromide were mixed in a polypropylene beaker to form a first mixture. 4.0 parts of (NH$_4$)$_8$[Mo$_{12}$CeO$_{42}$] hydrate were mixed with 8.0 parts of water with stirring in another polypropylene beaker to form a second mixture. 4.0 parts of a 50% sodium hydroxide solution were added to the second mixture. The two mixtures were mixed together with the result being the formation of a gel. The gel was stirred to homogenize the gel. The Si/Mo mole ratio was 8.8. The Si/Ce mole ratio was 105. The Si/Na mole ratio was 3.2. The mixture was divided into two equal samples, and each sample was placed in a Teflon-lined stainless steel bomb. The bombs were placed in an oven at a temperature of 150° C. The samples were recovered after 7 days and 14 days. The solids were recovered from the mother liquor by filtering. The solids were washed in water and in a 10% hydrochloric acid solution, then dried in air. The 7-day sample had the following analysis: 32% Si; 1.5% Ce; 0.37% Na; 0.09% Mo; and 0.05% Al. The mole ratios for this sample were: Si/Ce=107; Na/Ce=1.51; Mo/Ce=0.09; and Al/Ce=0.17. The X-ray diffraction pattern for the samples had the following significant lines (CuK$_\alpha$ radiation):

| Interplanar Spacing d(A) | Relative Intensity |
|---|---|
| 11.15 | s. |
| 9.95 | s. |
| 7.44 | w. |
| 6.37 | w. |
| 4.60 | w. |
| 3.83 | s. |
| 3.73 | s. |
| 3.65 | s. |

| Interplanar Spacing d(A) | Relative Intensity |
|---|---|
| 3.05 | w. |
| 2.00 | w. |

EXAMPLE 5

23.68 parts of Ludox AS-40 and 2.2 parts of tetrapropyl ammonium bromide (TPABr) were mixed in a polypropylene beaker to form a first mixture. 4.0 parts of $(NH_4)_8[Mo_{12}ThO_{42}]$ hydrate were mixed with 8.0 parts of water with stirring in another polypropylene beaker to form a second mixture. 4.0 parts of a 50% sodium hydroxide solution were added to the second mixture. The two mixtures were mixed together with the result being the formation of a gel. The gel was stirred to homogenize the gel. The Si/Mo mole ratio was 9. The Si/Th mole ratio was 107. The Si/TPABr mole ratio was 19.3. The Si/Na mole ratio was 3.2. The mixture was divided into two equal samples, and each sample was placed in a Teflon-lined stainless steel bomb. The bombs were placed in an oven at a temperature of 150° C. One sample was recovered after 7 days while the other was recovered after 14 days. The solids were recovered from the mother liquor by filtering. The solids were washed in water and a 10% hydrochloric acid solution, then dried in air. The 7-day sample had the following analysis: 32% Si; 3.5% Th; 0.38% Na; 0.05% Mo; and 0.04% Al. The mole ratios for this sample were: Si/Th=75; Na/Th=1.09; Mo/Th=0.03; and Al/Th=0.10. The X-ray diffraction pattern for the samples had the following significant lines (CuK$_\alpha$ radiation):

| Interplanar Spacing d(A) | Relative Intensity |
|---|---|
| 11.30 | s. |
| 10.09 | s. |
| 7.49 | w. |
| 6.41 | w. |
| 3.85 | s. |
| 3.73 | s. |
| 3.65 | s. |
| 3.05 | w. |
| 2.99 | w. |
| 2.00 | w. |

EXAMPLE 6

Two parts of the product of Example 2 were mixed with 100 parts of a 1M NH$_4$Cl solution for 10 hours with stirring at room temperature. The solids were recovered by filtration and thoroughly washed with water. The solids were pelletized and broken. 1.32 parts of the 10-30 mesh fraction of these solids were combined with 3.31 parts of inert silica-aluminum to provide a fixed catalyst bed having a volume of 5 cc. The catalyst bed was heated for 2 hours at 350° C. under a flow of 29 cc/min. of helium at atmospheric pressure. Methanol conversion runs were carried out at 350° C. and 450° C. by passing 1 cc of methanol per hour in a flow of 29 cc/min. of helium at atmospheric pressure over the catalyst bed. The results are summarized below. Selectivities are on a per carbon basis.

| | Run 1 | Run 2 |
|---|---|---|
| Temperature | 350° C. | 450° C. |
| Methanol Conversion | 22.5% | 35.8% |
| Carbon Monoxide | 1.4% | 10.5% |
| Carbon Dioxide | — | 1.2% |
| Dimethyl Ether | 61.9% | 44.7% |
| Methane | 7.2% | 25.2% |
| Ethane | — | 1.9% |
| Ethylene | — | 0.8% |
| Propylene | 11.3% | 4.8% |
| 1-Butene | 3.2% | 2.6% |
| Iso-Butylene | — | 2.4% |
| Trans-2-Butene | — | 1.7% |
| n-Butane | 3.6% | 1.1% |
| 1-Pentene | 5.9% | 1.5% |
| n-Pentane | 4.5% | 1.5% |

While the invention has been explained in relation to its preferred embodiment, it is to be understood that various modifications thereof will become apparent to those skilled in the art upon reading the specification. Therefore, it is to be understood that the invention disclosed herein is intended to cover such modifications as fall within the scope of the appended claims.

We claim:

1. A method for preparing a molecular sieving metallosilicate comprising the following steps:
   (A) providing a mixture comprising: (1) water; (2) an oxide of silicon source; (3) a synthesis directing agent and/or mineralizing agent; and (4) a tetravalent Lanthanide or Actinide series metal containing compound which is a heteropolymetallate of the formula

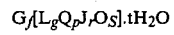

$G_f[L_g Q_p J_r O_s] \cdot t H_2O$ wherein
   G is an ion selected from the group consisting of hydrogen, Group I-A, II-A, I-B or II-B metals, ammonium, alkyl ammonium, alkyl phosphonium or alkyl arsonium, or a mixture of two or more thereof;
   L is P, As, Si, Ge, Al, H or a mixture of two or more thereof;
   Q is said tetravalent Lanthanide or Actinide series metal;
   J is Mo, W, V or Nb or a mixture of two or more thereof;
   f is a number which when multiplied by the charge of G will result in balancing the charge of the complex within the brackets;
   g is a number ranging from zero to about 20;
   p is a number ranging from zero to about 20;
   r is a number ranging from about 1 to about 50;
   s is a number ranging from about 7 to about 150; and
   t is a number ranging from zero to about 150: and
   (B) maintaining said mixture at a temperature in the range of about 80° C. to about 300° C. for an effective period of time to provide said metallosilicate.

2. The method of claim 1 with the step of separating said metallosilicate from its mother liquor.

3. The method of claim 1 with the step of washing said metallosilicate.

4. The method of claim 1 with the step of heat treating said metallosilicate in an inert, oxidizing or reducing atmosphere.

5. The method of claim 4 with step of cation exchanging said heat treated metallosilicate with an ammonium salt or the salt of a catalytically active metal to provide a cation exchanged metallosilicate.

6. The method of claim 5 with the step of heat treating said cation exchanged metallosilicate in an inert, oxidizing or reducing atmosphere.

7. The method of claim 1 wherein the mole ratio during step (A) of Si to said tetravalent Lanthanide or Actinide series metal is in the range of about 20 to about 200.

8. The method of claim 1 wherein the mole ratio during step (A) of $OH^-$ to Si is in the range of about 0.1 to about 10.

9. The method of claim 1 wherein the mole ratio during step (A) of $H_2O$ to $OH^-$ is in the range of about 10 to about 1000.

10. The method of claim 1 wherein the mole ratio of Si to said synthesis directing agent plus said mineralizing agent is in the range of about 0.1 to about 30.

11. The method of claim 1 wherein said synthesis directing agent is the cation of an amine or alkanol amine compound, alkyl substituted amine or alkyl substituted alkanol amine compound, ammonium or alkyl ammonium compound, or alkyl phosphonium or alkyl arsonium compound.

12. The method of claim 11 wherein said alkyl ammonium compound is a mono-, di-, tri- or tetra-alkyl ammonium compound, each alkyl group having up to about six carbon atoms.

13. The method of claim 1 wherein said synthesis directing agent is a salt or hydroxide of tetrapropyl ammonium.

14. The method of claim 1 wherein said mineralizing agent is an oxide, hydroxide or salt of an alkali or alkaline earth metal.

15. The method of claim 1 wherein said mineralizing agent is sodium hydroxide.

16. The method of claim 1 wherein said mixture is maintained in an enclosed container under at least the vapor pressure of water during step (B).

17. The method of claim 1 wherein G is a hydrogen, ammonium or alkali metal ion, or a mixture thereof.

18. The method of claim 1 wherein g is zero; r is 12; s is 42; J is Mo or W; Q is Ce, Th, U, Pr or a mixture thereof; and p is 1.

19. The method of claim 1 wherein L is P, Ge or a mixture thereof; J is Mo or W; Q is Ce, Pr, Tb, Th, Pa, U, Np, Pu, Am or a mixture of two or more thereof; g is 2; r is 22; p is 1; and s is 78.

20. The method of claim 1 wherein L is P, Ge or a mixture thereof; g is 4; J is Mo or W; r is 34; Q is Ce, Pr, Tb, Th, Pa, U, Np, Pu, Am or a mixture of two or more thereof; p is 1; and s is 122.

21. The method of claim 1 wherein the temperature during step (B) is in the range of about 125° C. to about 200° C.

22. The method of claim 1 wherein the time period for step (B) is from about 4 hours to about 30 days.

23. The method of claim 1 wherein the time period for step (B) is from about one to about ten days.

24. The method of claim 1 wherein said metallosilicate can be represented by the formula:

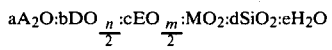

$$aA_2O:bDO_{\frac{n}{2}}:cEO_{\frac{m}{2}}:MO_2:dSiO_2:eH_2O$$

wherein

A is an ammonium, alkyl ammonium, alkyl phosphonium or alkyl arsoninum ion;

D is an alkali or alkaline earth metal ion, or a mixture of two or more thereof;

E is selected from the group consisting of Al, B, Mo, W, Fe, or a mixture of two or more thereof;

M is a tetravalent metal selected from the Lanthanide or Actinide series;

a is a number ranging from zero to about 25;

b is a number ranging from zero to about 1.5;

c is a number ranging from zero to about 0.3;

d is a number ranging from about 20 to about 500;

e is a number ranging from zero to about 200;

the X-ray diffraction pattern from said metallosilicate as synthesized showing at least the following significant lines:

| Interplanar Spacing d(A) | Relative Intensity |
|---|---|
| 11.25 ± 0.2 | s. |
| 10.1 ± 0.2 | m.–s. |
| 7.55 ± 0.15 | w. |
| 6.40 ± 0.10 | w. |
| 4.61 ± 0.08 | w. |
| 3.84 ± 0.08 | s. |
| 3.73 ± 0.05 | s. |
| 3.65 ± 0.05 | m.–s. |
| 3.05 ± 0.03 | w. |
| 2.99 ± 0.02 | w. |
| 2.00 ± 0.02 | w. |

25. The method of claim 24 wherein a is in the range of from zero to about 12.

26. The method of claim 1 wherein c is in the range of from zero to about 0.2.

27. The method of claim 24 wherein d is in the range of from about 30 to about 200.

28. The method of claim 24 wherein e is in the range of from zero to about 80.

29. The method of claim 24 wherein M is Ce, Th, U, Pr, Tb, Pa, Np, Pu, Am or a mixture of two or more thereof.

30. The method of claim 24 wherein M is Ce, Th, Pr, U or a mixture of two or more thereof.

31. The method of claim 24 wherein A is tetrapropylammonium.

32. The method of claim 24 wherein D is sodium.

* * * * *